United States Patent
Ceniccola et al.

(10) Patent No.: US 10,335,130 B2
(45) Date of Patent: *Jul. 2, 2019

(54) SURGICAL RETRIEVAL APPARATUS

(71) Applicant: Covidien LP, Mansfield, MA (US)

(72) Inventors: Anthony L. Ceniccola, Hamden, CT (US); Margaret Uznanski, Philadelphia, PA (US); Mark Peter Rogers, Swaffam Bulbeck (GB); Brandon Wesley Craft, Phoenix, MD (US); Natalie Scott, Cambridge (GB); Nicholas John Collier, Burwell (GB); Charlotte Adele Clark, Cambridge (GB)

(73) Assignee: Covidien LP, Mansfield, MA (US)

( * ) Notice: Subject to any disclaimer, the term of this patent is extended or adjusted under 35 U.S.C. 154(b) by 475 days.

This patent is subject to a terminal disclaimer.

(21) Appl. No.: 15/155,381

(22) Filed: May 16, 2016

(65) Prior Publication Data
US 2016/0256145 A1 Sep. 8, 2016

Related U.S. Application Data

(63) Continuation of application No. 12/579,497, filed on Oct. 15, 2009, now Pat. No. 9,370,341.
(Continued)

(51) Int. Cl.
*A61B 17/221* (2006.01)
*A61B 17/00* (2006.01)
(Continued)

(52) U.S. Cl.
CPC ...... *A61B 17/00234* (2013.01); *A61B 17/221* (2013.01); *A61B 2017/00287* (2013.01);
(Continued)

(58) Field of Classification Search
CPC ........ A61B 17/00234; A61B 17/32056; A61B 17/22–2258; A61B 17/221; A61B 17/26;
(Continued)

(56) References Cited

U.S. PATENT DOCUMENTS 30,471 A 10/1860 Dudley
35,164 A 5/1862 Logan et al.
(Continued)

FOREIGN PATENT DOCUMENTS

DE 3542667 A1 6/1986
DE 8435489 U1 8/1986
(Continued)

OTHER PUBLICATIONS

Partial International Search Report corresponding to EP 12191639. 9, dated Feb. 20, 2013; 6 pp.
(Continued)

*Primary Examiner* — Jonathan A Hollm

(57) ABSTRACT

A surgical retrieval apparatus includes an elongate tubular member having a drive rod slidably disposed therein. A support member is operably coupled to a distal end of the drive rod. A pouch is attached to the support member and has a closed end and an open end. The pouch may be releasably coupled to the support member. An end effector is repositionable with respect to a longitudinal axis of the tubular member. The support member may include an expandable member.

18 Claims, 14 Drawing Sheets

Related U.S. Application Data

(60) Provisional application No. 61/107,745, filed on Oct. 23, 2008.

(51) Int. Cl.
*A61B 17/29* (2006.01)
*A61B 90/00* (2016.01)

(52) U.S. Cl.
CPC .............. *A61B 2017/00557* (2013.01); *A61B 2017/00898* (2013.01); *A61B 2017/00907* (2013.01); *A61B 2017/2212* (2013.01); *A61B 2017/2905* (2013.01); *A61B 2017/2927* (2013.01); *A61B 2090/037* (2016.02); *A61B 2217/005* (2013.01); *A61B 2217/007* (2013.01)

(58) Field of Classification Search
CPC ........... A61B 2017/00287; A61B 2017/00358; A61B 2017/22001–2253; A61B 2017/2212–2217
See application file for complete search history.

(56) References Cited

U.S. PATENT DOCUMENTS

| | | | |
|---|---|---|---|
| 156,477 | A | 11/1874 | Bradford |
| 1,609,014 | A | 11/1926 | Dowd |
| 3,800,781 | A | 4/1974 | Zalucki |
| 4,557,255 | A | 12/1985 | Goodman |
| 4,611,594 | A | 9/1986 | Grayhack et al. |
| 4,744,363 | A | 5/1988 | Hasson |
| 4,790,812 | A | 12/1988 | Hawkins, Jr. et al. |
| 4,852,586 | A | 8/1989 | Haines |
| 4,927,427 | A | 5/1990 | Kriauciunas et al. |
| 4,977,903 | A | 12/1990 | Haines |
| 4,991,593 | A | 2/1991 | LeVahn |
| 4,997,435 | A | 3/1991 | Demeter |
| 5,037,379 | A | 8/1991 | Clayman et al. |
| 5,074,867 | A | 12/1991 | Wilk |
| 5,084,054 | A | 1/1992 | Bencini et al. |
| 5,143,082 | A | 9/1992 | Kindberg et al. |
| 5,147,371 | A | 9/1992 | Washington et al. |
| 5,176,687 | A | 1/1993 | Hasson et al. |
| 5,190,542 | A | 3/1993 | Nakao et al. |
| 5,190,555 | A | 3/1993 | Wetter et al. |
| 5,190,561 | A | 3/1993 | Graber |
| 5,192,284 | A | 3/1993 | Pleatman |
| 5,192,286 | A | 3/1993 | Phan et al. |
| 5,201,740 | A | 4/1993 | Nakao et al. |
| 5,215,521 | A | 6/1993 | Cochran et al. |
| 5,224,930 | A | 7/1993 | Spaeth et al. |
| 5,234,439 | A | 8/1993 | Wilk et al. |
| 5,279,539 | A | 1/1994 | Bohan et al. |
| 5,312,416 | A | 5/1994 | Spaeth et al. |
| 5,330,483 | A | 7/1994 | Heaven et al. |
| 5,336,227 | A | 8/1994 | Nakao et al. |
| 5,337,754 | A * | 8/1994 | Heaven ............ A61B 17/00234 128/DIG. 24 |
| 5,341,815 | A | 8/1994 | Cofone et al. |
| 5,352,184 | A | 10/1994 | Goldberg et al. |
| 5,354,303 | A | 10/1994 | Spaeth et al. |
| 5,368,545 | A | 11/1994 | Schaller et al. |
| 5,368,597 | A | 11/1994 | Pagedas |
| 5,370,647 | A | 12/1994 | Graber et al. |
| 5,383,888 | A | 1/1995 | Zvenyatsky et al. |
| 5,423,830 | A | 6/1995 | Schneebaum et al. |
| 5,443,472 | A | 8/1995 | Li |
| 5,465,731 | A | 11/1995 | Bell et al. |
| 5,480,404 | A | 1/1996 | Kammerer et al. |
| 5,484,451 | A | 1/1996 | Akopov et al. |
| 5,486,182 | A | 1/1996 | Nakao et al. |
| 5,486,183 | A | 1/1996 | Middleman et al. |
| 5,499,988 | A | 3/1996 | Espiner et al. |
| 5,524,633 | A | 6/1996 | Heaven et al. |
| 5,535,759 | A | 7/1996 | Wilk |
| 5,578,048 | A | 11/1996 | Pasqualucci et al. |
| 5,611,803 | A | 3/1997 | Heaven et al. |
| 5,618,294 | A | 4/1997 | Aust et al. |
| 5,618,296 | A | 4/1997 | Sorensen et al. |
| 5,630,822 | A | 5/1997 | Hermann et al. |
| 5,642,282 | A | 6/1997 | Sonehara |
| 5,643,282 | A | 7/1997 | Kieturakis |
| 5,643,283 | A | 7/1997 | Younker |
| 5,645,083 | A | 7/1997 | Essig et al. |
| 5,647,372 | A | 7/1997 | Tovey et al. |
| 5,649,902 | A | 7/1997 | Yoon |
| 5,658,296 | A | 8/1997 | Bates et al. |
| 5,679,423 | A | 10/1997 | Shah |
| 5,735,289 | A | 4/1998 | Pfeffer et al. |
| 5,743,456 | A | 4/1998 | Jones et al. |
| 5,755,724 | A | 5/1998 | Yoon |
| 5,759,187 | A | 6/1998 | Nakao et al. |
| 5,769,794 | A | 6/1998 | Conlan et al. |
| 5,785,677 | A | 7/1998 | Auweiler |
| 5,788,709 | A | 8/1998 | Riek et al. |
| 5,792,145 | A | 8/1998 | Bates et al. |
| 5,814,044 | A | 9/1998 | Hooven |
| 5,829,440 | A | 11/1998 | Broad, Jr. |
| 5,836,953 | A | 11/1998 | Yoon |
| 5,853,374 | A | 12/1998 | Hart et al. |
| 5,895,392 | A | 4/1999 | Riek et al. |
| 5,906,621 | A | 5/1999 | Secrest et al. |
| 5,908,429 | A | 6/1999 | Yoon |
| 5,944,727 | A | 8/1999 | Ahari et al. |
| 5,957,884 | A | 9/1999 | Hooven |
| 5,971,995 | A | 10/1999 | Rousseau |
| 5,980,544 | A | 11/1999 | Vaitekunas |
| 5,997,547 | A | 12/1999 | Nakao et al. |
| 6,004,330 | A | 12/1999 | Middleman et al. |
| 6,007,512 | A | 12/1999 | Hooven |
| 6,007,546 | A | 12/1999 | Snow et al. |
| 6,019,770 | A | 2/2000 | Christoudias |
| 6,036,681 | A | 3/2000 | Hooven |
| 6,059,793 | A | 5/2000 | Pagedas |
| 6,123,701 | A | 9/2000 | Nezhat |
| 6,152,932 | A | 11/2000 | Ternstrom |
| 6,162,235 | A | 12/2000 | Vaitekunas |
| 6,165,121 | A | 12/2000 | Alferness |
| 6,168,603 | B1 | 1/2001 | Leslie et al. |
| 6,228,095 | B1 | 5/2001 | Dennis |
| 6,270,505 | B1 | 8/2001 | Yoshida et al. |
| 6,277,083 | B1 | 8/2001 | Eggers et al. |
| 6,280,450 | B1 | 8/2001 | McGuckin, Jr. |
| 6,344,026 | B1 | 2/2002 | Burbank et al. |
| 6,348,056 | B1 | 2/2002 | Bates et al. |
| 6,350,266 | B1 | 2/2002 | White et al. |
| 6,350,267 | B1 | 2/2002 | Stefanchik |
| 6,383,195 | B1 | 5/2002 | Richard |
| 6,383,196 | B1 | 5/2002 | Leslie et al. |
| 6,383,197 | B1 | 5/2002 | Conlon et al. |
| 6,406,440 | B1 | 6/2002 | Stefanchik |
| 6,409,733 | B1 | 6/2002 | Conlon et al. |
| 6,419,639 | B2 | 7/2002 | Walther et al. |
| 6,447,523 | B1 | 9/2002 | Middleman et al. |
| 6,471,659 | B2 | 10/2002 | Eggers et al. |
| 6,506,166 | B1 | 1/2003 | Hendler et al. |
| 6,508,773 | B2 | 1/2003 | Burbank et al. |
| 6,537,273 | B1 | 3/2003 | Sosiak et al. |
| 6,589,252 | B2 | 7/2003 | McGuckin, Jr. |
| 6,752,811 | B2 | 6/2004 | Chu et al. |
| 6,755,779 | B2 | 6/2004 | Vanden Hoek et al. |
| 6,780,193 | B2 | 8/2004 | Leslie et al. |
| 6,805,699 | B2 | 10/2004 | Shimm |
| 6,840,948 | B2 | 1/2005 | Albrecht et al. |
| 6,872,211 | B2 | 3/2005 | White et al. |
| 6,887,255 | B2 | 5/2005 | Shimm |
| 6,994,696 | B2 | 2/2006 | Suga |
| 7,052,454 | B2 | 5/2006 | Taylor |
| 7,052,501 | B2 | 5/2006 | McGuckin, Jr. |
| 7,090,637 | B2 | 8/2006 | Danitz et al. |
| 7,115,125 | B2 | 10/2006 | Nakao et al. |
| 7,270,663 | B2 | 9/2007 | Nakao |
| 7,273,488 | B2 | 9/2007 | Nakamura et al. |
| 7,325,546 | B2 | 2/2008 | Burbank et al. |
| 7,410,491 | B2 | 8/2008 | Hopkins et al. |

(56) References Cited

U.S. PATENT DOCUMENTS

| | | |
|---|---|---|
| 7,547,310 B2 | 6/2009 | Whitfield |
| 7,670,346 B2 | 3/2010 | Whitfield |
| 7,762,959 B2 | 7/2010 | Bilsbury |
| 7,819,121 B2 | 10/2010 | Amer |
| 8,579,914 B2 | 11/2013 | Menn et al. |
| 9,370,341 B2 | 6/2016 | Ceniccola et al. |
| 2002/0068943 A1 | 6/2002 | Chu et al. |
| 2002/0082516 A1 | 6/2002 | Stefanchik |
| 2003/0073970 A1 | 4/2003 | Suga |
| 2003/0100909 A1 | 5/2003 | Suzuki |
| 2003/0100919 A1 | 5/2003 | Hopkins et al. |
| 2003/0199915 A1 | 10/2003 | Shimm |
| 2003/0216773 A1 | 11/2003 | Shimm |
| 2004/0054353 A1 | 3/2004 | Taylor |
| 2004/0097960 A1 | 5/2004 | Terachi et al. |
| 2004/0111113 A1 | 6/2004 | Nakamura et al. |
| 2004/0138587 A1 | 7/2004 | Lyons |
| 2004/0193212 A1* | 9/2004 | Taniguchi ............... A61B 17/29 606/205 |
| 2004/0236316 A1 | 11/2004 | Danitz et al. |
| 2005/0054945 A1 | 3/2005 | Cohen et al. |
| 2005/0085808 A1 | 4/2005 | Nakao |
| 2005/0165411 A1 | 7/2005 | Orban |
| 2005/0267492 A1* | 12/2005 | Poncet ................ A61B 17/221 606/114 |
| 2006/0030750 A1 | 2/2006 | Amer |
| 2006/0052799 A1 | 3/2006 | Middleman et al. |
| 2006/0058776 A1 | 3/2006 | Bilsbury |
| 2006/0169287 A1 | 8/2006 | Harrison et al. |
| 2006/0199999 A1 | 9/2006 | Ikeda et al. |
| 2006/0200169 A1 | 9/2006 | Sniffin |
| 2006/0200170 A1 | 9/2006 | Aranyi |
| 2006/0229639 A1 | 10/2006 | Whitfield |
| 2006/0229640 A1 | 10/2006 | Whitfield |
| 2006/0235512 A1 | 10/2006 | Osborne et al. |
| 2007/0016224 A1 | 1/2007 | Nakao |
| 2007/0016225 A1 | 1/2007 | Nakao |
| 2007/0073251 A1 | 3/2007 | Zhou et al. |
| 2007/0088370 A1 | 4/2007 | Kahle et al. |
| 2007/0135780 A1 | 6/2007 | Pagedas |
| 2007/0135781 A1 | 6/2007 | Hart |
| 2007/0158385 A1 | 7/2007 | Hueil et al. |
| 2007/0186935 A1 | 8/2007 | Wang et al. |
| 2008/0177214 A1 | 7/2008 | Robertsson et al. |
| 2008/0188766 A1 | 8/2008 | Gertner |
| 2008/0221588 A1 | 9/2008 | Hollis et al. |
| 2008/0234696 A1 | 9/2008 | Taylor et al. |
| 2008/0300613 A1 | 12/2008 | Shelton, IV et al. |
| 2008/0300621 A1 | 12/2008 | Hopkins et al. |
| 2008/0312496 A1 | 12/2008 | Zwolinski |
| 2009/0082779 A1 | 3/2009 | Nakao |
| 2009/0182292 A1 | 7/2009 | Egle et al. |
| 2009/0192510 A1 | 7/2009 | Bahney |
| 2009/0192518 A1 | 7/2009 | Golden et al. |
| 2009/0240238 A1 | 9/2009 | Grodrian et al. |
| 2009/0299143 A1* | 12/2009 | Conlon ................. A61B 17/29 600/153 |
| 2010/0000471 A1 | 1/2010 | Hibbard |
| 2011/0184434 A1 | 7/2011 | Parihar et al. |
| 2011/0184436 A1 | 7/2011 | Shelton, IV et al. |
| 2011/0190781 A1 | 8/2011 | Collier et al. |
| 2011/0299799 A1 | 12/2011 | Towe |
| 2012/0046667 A1 | 2/2012 | Cherry et al. |
| 2012/0083795 A1 | 4/2012 | Fleming et al. |
| 2013/0023895 A1 | 1/2013 | Saleh |

FOREIGN PATENT DOCUMENTS

| | | |
|---|---|---|
| DE | 4204210 A1 | 8/1992 |
| DE | 19624826 A1 | 1/1998 |
| EP | 0947166 A2 | 10/1999 |
| EP | 1685802 A1 | 8/2006 |
| EP | 1707126 A1 | 10/2006 |
| EP | 2005900 A2 | 12/2008 |
| EP | 2184014 A2 | 5/2010 |
| EP | 2353510 A2 | 8/2011 |
| FR | 1272412 A | 9/1961 |
| GB | 2460099 A | 11/2009 |
| WO | 9315675 A1 | 8/1993 |
| WO | 9509666 A1 | 4/1995 |
| WO | 01/35831 A1 | 5/2001 |
| WO | 2004002334 A1 | 1/2004 |
| WO | 2004/112571 A2 | 12/2004 |
| WO | 2005/112783 A1 | 12/2005 |
| WO | 2006/110733 | 10/2006 |
| WO | 2007/048078 A1 | 4/2007 |
| WO | 2007/048085 A2 | 4/2007 |
| WO | 2008/114234 A2 | 9/2008 |
| WO | 2009055791 A2 | 4/2009 |
| WO | 2009/149146 A1 | 12/2009 |
| WO | 2011/090862 A2 | 7/2011 |

OTHER PUBLICATIONS

Extended European Search Report corresponding to EP No. 11 25 0837.9, completed Sep. 3, 2013 and dated Sep. 10, 2013; (7 pp).
Extended European Search Report corresponding to EP No. 11 25 0838.7, completed Sep. 3, 2013 and dated Sep. 10, 2013; (5 pp).
Partial International Search Report corresponding to EP No. 12 19 1639.9, dated Feb. 20, 2013; (6 pp).
Extended European Search Report corresponding to EP No. 13 17 0118.7. completed Nov. 25, 2013 and dated Dec. 5, 2013; (10 pp).
International Search Report corresponding to European Application No. EP 12 16 5852 completed Jun. 13, 2012 and dated Jun. 20, 2012.
http://www.biomaterials.org/week/bio17.cfm, definition and examples of hydrogels, Jun. 1, 2007.
European Search Report EP 12150271 dated Jan. 14, 2013.
European Search Report EP 12193450 dated Feb. 27, 2013.
European Search Report EP 12189517.1 dated Mar. 6, 2013.
European Search Report EP 12158873 dated Jul. 19, 2012.
European Search Report EP 11250836 dated Sep. 12, 2013.
European Search Report EP 11250114.3 dated Feb. 10, 2014.
European Office Action dated Apr. 14, 2016, issued in European Application No. 09 252 474.3.

* cited by examiner

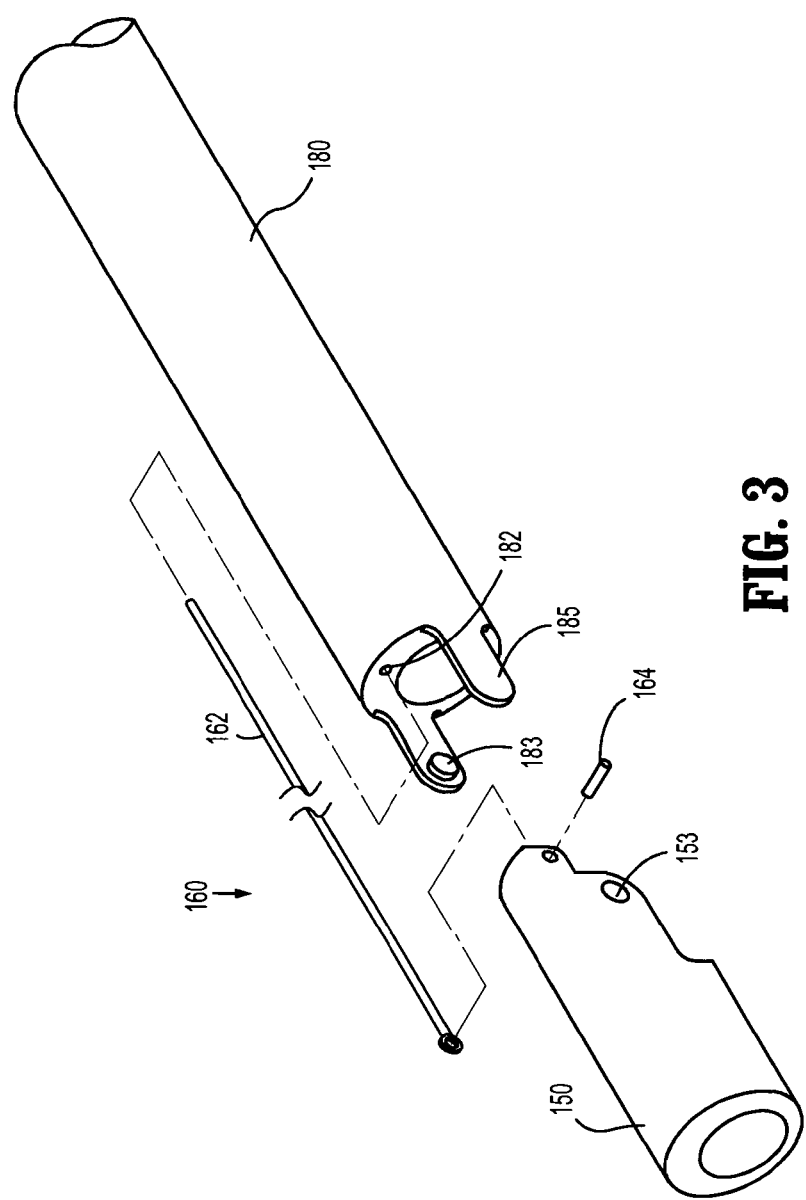

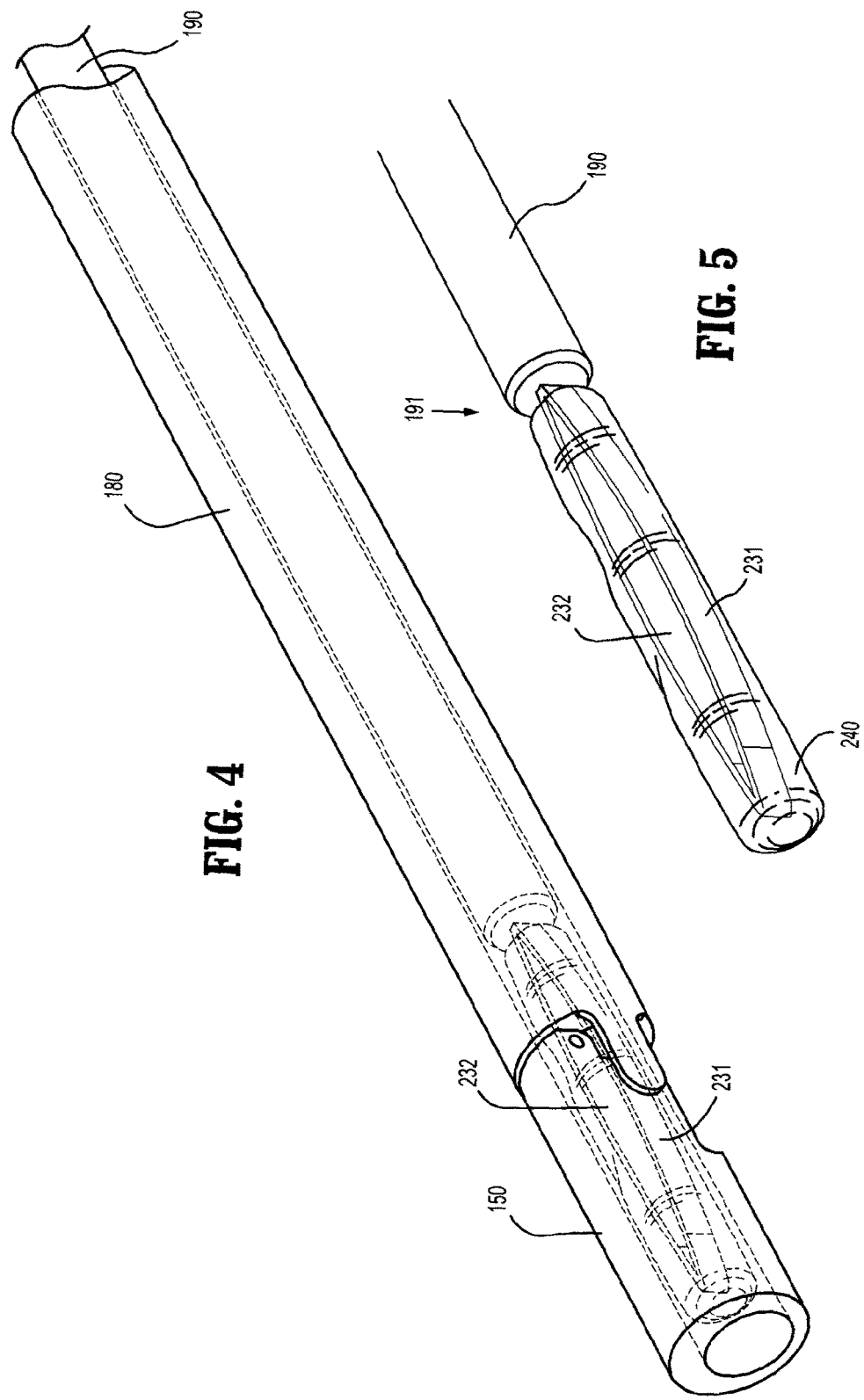

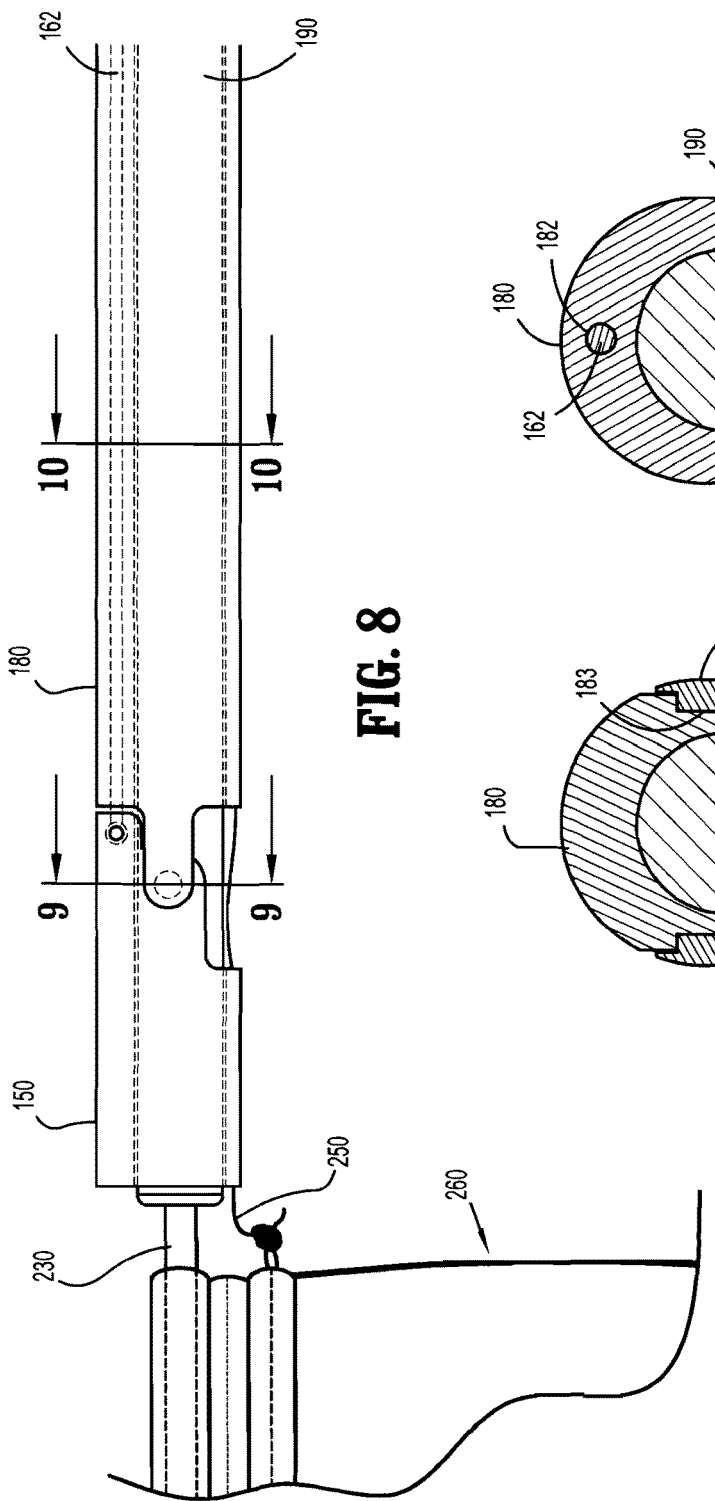

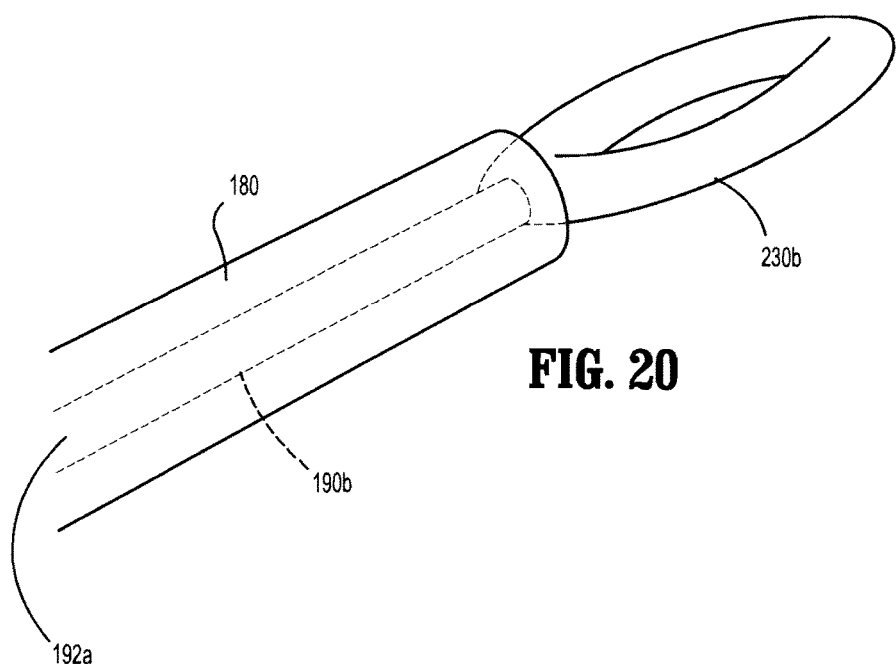
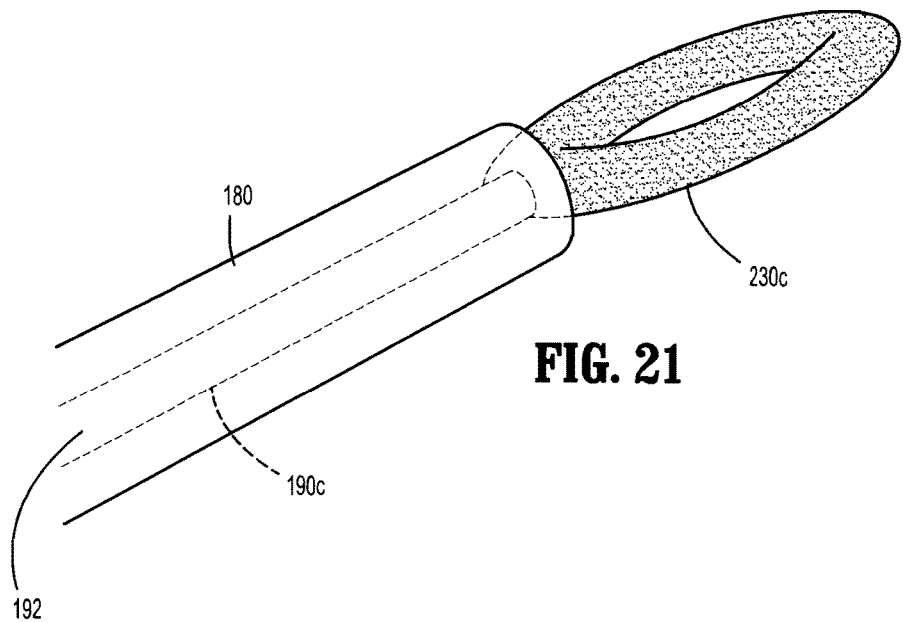

SURGICAL RETRIEVAL APPARATUS

CROSS-REFERENCE TO RELATED APPLICATIONS

This application is a Continuation of U.S. patent application Ser. No. 12/579,497 filed Oct. 15, 2009, which claims benefit of and priority to U.S. Provisional Application No. 61/107,745 filed Oct. 23, 2008, and the disclosures of each of the above-identified applications are hereby incorporated by reference in their entirety.

BACKGROUND

1. Technical Field

The present disclosure relates to a surgical containment apparatus. More particularly, the present disclosure relates to a specimen retrieval apparatus and method for use in minimally invasive surgical procedures.

2. Background of Related Art

Laparoscopic and endoscopic surgical procedures are minimally invasive procedures in which operations are carried out within the body by using elongated instruments inserted through small entrance openings in the body. The initial opening in the body tissue to allow passage of the endoscopic or laparoscopic instruments to the interior of the body may be a natural passageway of the body, or it can be created by a tissue piercing instrument such as a trocar. Laparoscopic and endoscopic procedures generally require that any instrumentation inserted in the body be sealed, i.e. provisions must be made to ensure that gases do not enter or exit the body through the instrument or the entrance incision so that the surgical region of the body, e.g. the peritoneum, may be insufflated. Mechanical actuation of such instruments is for the most part constrained to the movement of the various components along a longitudinal axis with structure provided to convert longitudinal movement to lateral movement where necessary.

Because the endoscopic or laparoscopic tubes, instrumentation, and any required punctures or incisions are relatively narrow, endoscopic or laparoscopic surgery is less invasive as compared to conventional surgical procedures in which the surgeon is required to cut open large areas of body tissue. Therefore, laparoscopic or endoscopic surgery minimizes trauma to the patient and reduces patient recovery time.

Minimally invasive procedures may be used for partial or total removal of body tissue or organs from the interior of the body, e.g. nephrectomy, cholecystectomy, and other procedures including thoracic procedures. During such procedures, it is common that a cyst, tumor, or other affected tissue or organ must be removed via the access opening in the skin, or through a cannula. Various types of entrapment devices have been disclosed to facilitate this procedure. In many procedures where cancerous tumors are removed, removal of the specimen in an enclosed environment is highly desirable to prevent seeding.

U.S. Pat. No. 5,037,379 to Clayman et al. discloses a surgical tissue bag for percutaneously debulking tissue by morcellation. The bag includes a layer of puncture-resistant material, a layer of moisture-resistant material and a drawstring. In a disclosed method of use, the bag is placed within the body cavity, the body tissue or organ is placed within the bag, the opening of the bag is pulled through the incision in the skin leaving the distal end of the bag containing the tissue or organ within the body cavity, a morcellator is then inserted into the bag, and then the tissue or organ is debulked and suctioned out of the bag.

U.S. Pat. No. 5,074,867 to Wilk discloses a planar membrane having filaments attached to its corners. The membrane is placed within a body cavity with the filaments extending through the trocar cannula to the outside of the body. The organ or tissue to be removed is placed on the membrane and the filaments are pulled to close the membrane around the organ and draw it through the cannula, if the organ is sufficiently deformable. If the organ is not sufficiently deformable, e.g. because of the presence of gallstones, a forceps or other instrument is used to crush the stones or tissue.

Improvements to prior art entrapment devices are disclosed in U.S. Pat. No. 5,647,372 to Tovey et al. and in U.S. Pat. No. 5,465,731 to Bell et al., the disclosures of which are hereby incorporated by reference in their entirety. It would be advantageous to provide a retrieval device with increased maneuverability. Additionally, for certain procedures it might be advantageous to provide a retrieval device which reduces trauma to surrounding tissue.

SUMMARY

The present disclosure is directed to a surgical retrieval apparatus. The presently disclosed surgical retrieval apparatus includes an elongate tubular member having a proximal end, a distal end, and a bore extending therebetween. An end effector is disposed at the distal end of the elongate tubular member. The end effector is repositionable between a first position that is substantially aligned with a longitudinal axis of the elongate tubular member and a second position that defines an acute angle with respect to the longitudinal axis. A support member is movable between a retracted position and a distal position at least partially exterior to the end effector. The support member includes at least one section having a generally arcuate configuration when in a deployed state. A pouch is removably attached to the support member. The pouch has a first end that is transitionable between an open configuration and a closed configuration. A drive member is slidably disposed within the bore of the tubular member for moving the support member from the proximal position to the distal position.

In one embodiment, at least a portion of the elongate tubular member is flexible. The surgical retrieval apparatus may also include an articulation assembly positioned between the distal end of the elongate tubular member and the end effector. The articulation assembly may include a plurality of movable segments.

The surgical retrieval apparatus may also include a handle at a proximal end of the elongate tubular member. The handle may include a switch for repositioning the end effector between the first and second positions. A drawstring can extend from the handle to the pouch wherein proximal movement of the drawstring closes the mouth of the pouch. The drawstring may also be configured such that additional proximal movement separates the pouch from the support member. The support member can be rotatable about the longitudinal axis of the elongate tubular member.

In one embodiment, the support member may be an expandable member that transitions from a collapsed state to an expanded state. The expandable member may be coupled to a source of fluid and/or vacuum. An expandable foam may be used in the support member.

In another aspect of the present disclosure, a surgical retrieval apparatus is provided comprising an elongate tubular member having an open distal end and a bore, a drive member slidably disposed in the bore, and a support member coupled to the drive member. The support member is movable between a proximal position and a distal position at least partially exterior to the elongate tubular member in response to axial movement of the drive member, the support member including an expandable member having a chamber. The expandable member transitions from a first condition to a second condition upon introduction of a fluid to the chamber. A pouch extends from the support member and has a first end and a closed second end, the first end transitionable between open and closed configurations when the expandable member transitions between the first condition and the second condition.

The expandable member preferably transitions from the second condition to the first condition upon removal of the fluid from the chamber of the expandable member. In one embodiment, the expandable member includes an expandable foam.

A method of retrieving a tissue sample is also disclosed comprising inserting the surgical retrieval apparatus through an opening in a patient's skin. After the surgical retrieval apparatus enters the operative site, the practitioner positions the pouch in proximity to the tissue sample and moves the tissue sample into the pouch through the first end of the pouch. Subsequently, the practitioner closes the first end of the pouch and removes the surgical retrieval apparatus through the opening. The practitioner may also separate the pouch from the support member prior to removing the surgical retrieval apparatus. The pouch and tissue sample may be removed through a second access device located in a second opening in the patient's skin. In one embodiment, the retrieval apparatus is inserted through an access port into the thoracic cavity.

BRIEF DESCRIPTION OF THE DRAWINGS

Embodiments of the presently disclosed specimen retrieval apparatus are described hereinbelow with reference to the drawings wherein:

FIG. 3 is an enlarged view of detail area "3" in FIG. 2 illustrating an articulation assembly;

FIG. 4 is a perspective view of a distal end of the specimen retrieval apparatus of FIG. 1 showing a support member coupled to a drive rod;

FIG. 5 is a perspective view of the spring and drive rod of FIG. 4 with a cover disposed about the support member;

FIG. 8 is a side view of the distal end of the specimen retrieval apparatus of FIG. 1 with the retrieval pouch in the deployed state and the articulation assembly in a first state;

FIG. 9 is an end cross-sectional view taken along section line 9-9 of FIG. 8;

FIG. 10 is an end cross-sectional view taken along section line 10-10 of FIG. 8;

FIG. 20 is a perspective view of a distal end of an embodiment of the presently disclosed specimen retrieval apparatus illustrating an alternate support member assembly;

FIG. 21 is a perspective view of a distal end of an embodiment of the presently disclosed specimen retrieval apparatus illustrating another alternate support member assembly;

DETAILED DESCRIPTION OF THE EMBODIMENTS

Figure 1:
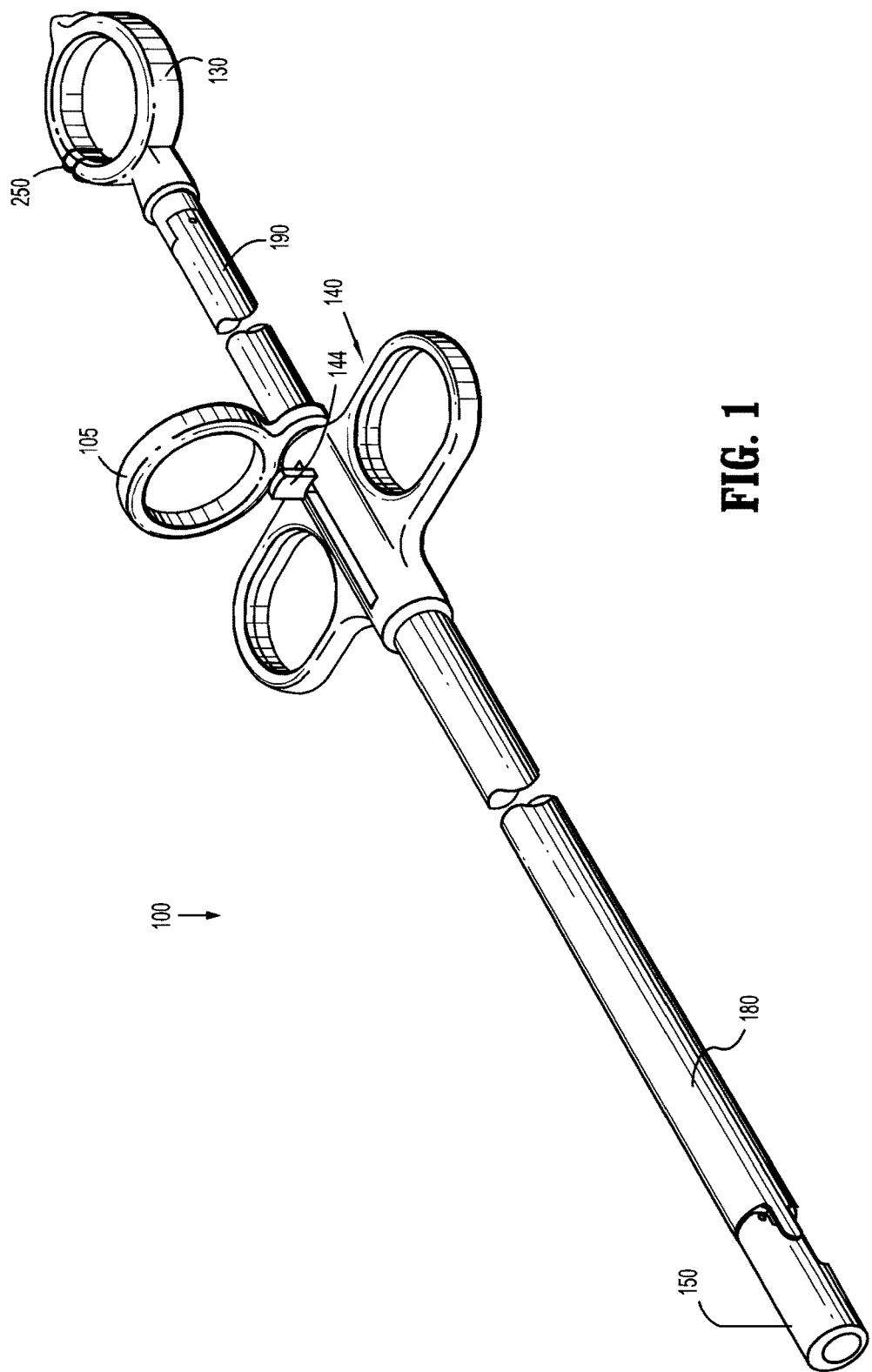
FIG. 1 is a perspective view of the specimen retrieval apparatus according to an embodiment of the present disclosure.

Embodiments of the present disclosure will now be described in detail with reference to the drawings, in which like reference numerals designate identical or corresponding elements in each of the several views. As used herein, the term distal refers to the portion of the instrument which is further from the user while, the term proximal refers to that portion of the instrument which is closer to the user. In the following description, well-known functions or constructions are not described in detail to avoid obscuring the present disclosure in unnecessary detail.

As used herein with reference to the present disclosure, the terms laparoscopic and endoscopic are interchangeable and refer to instruments having a relatively narrow operating portion for insertion into a cannula or a small incision in the skin. They also refer to minimally invasive surgical procedures. It is believed that the present disclosure may find use in any procedure where access to the interior of the body is limited to a relatively small incision, with or without the use of a cannula as in minimally invasive procedures. The devices herein may find particular use in minimally invasive thoracic surgery where access to the thoracic cavity is through a space located between adjacent ribs known as the intercostal space.

Figure 2:
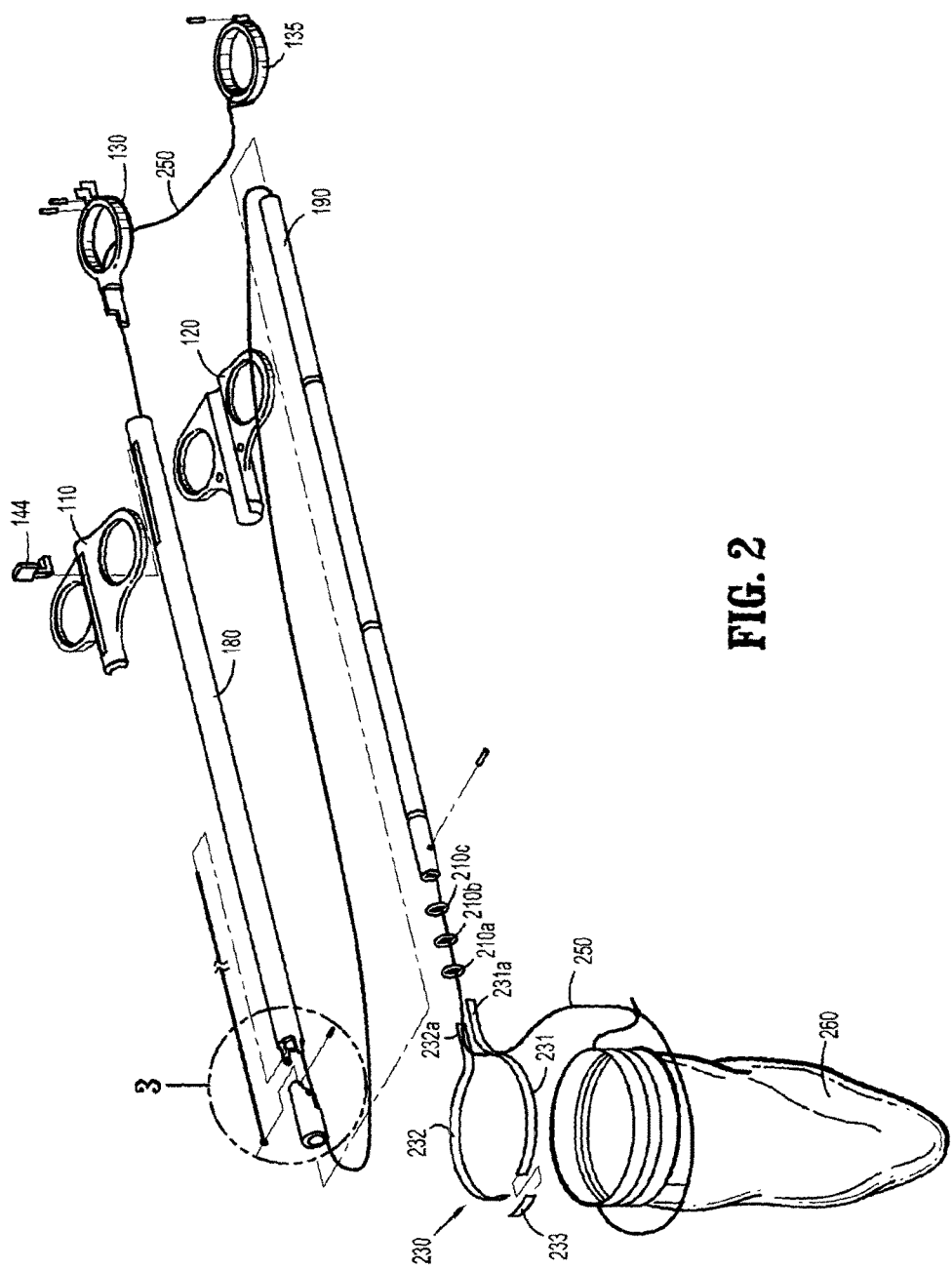
FIG. 2 is an exploded perspective view, with parts separated, of the specimen retrieval apparatus of FIG. 1.

Referring initially to FIGS. 1 and 2, a surgical retrieval apparatus 100 is illustrated. Surgical retrieval apparatus 100 is preferably configured and dimensioned for use in minimally invasive surgical procedures (e.g. laparoscopic, endoscopic, and thoracic procedures). Surgical retrieval apparatus 100 includes an elongated tubular member 180, a handle 140, a finger loop 130 for engagement by a user's finger, a drive rod 190, and an end effector 150. Handle 140 includes handle portions 110, 120 and a slidable switch 144. In one embodiment, end effector 150 is coupled to a distal end of tubular member 180 using an articulation assembly 160 (FIG. 3) that will be described in detail below.

Figure 7:
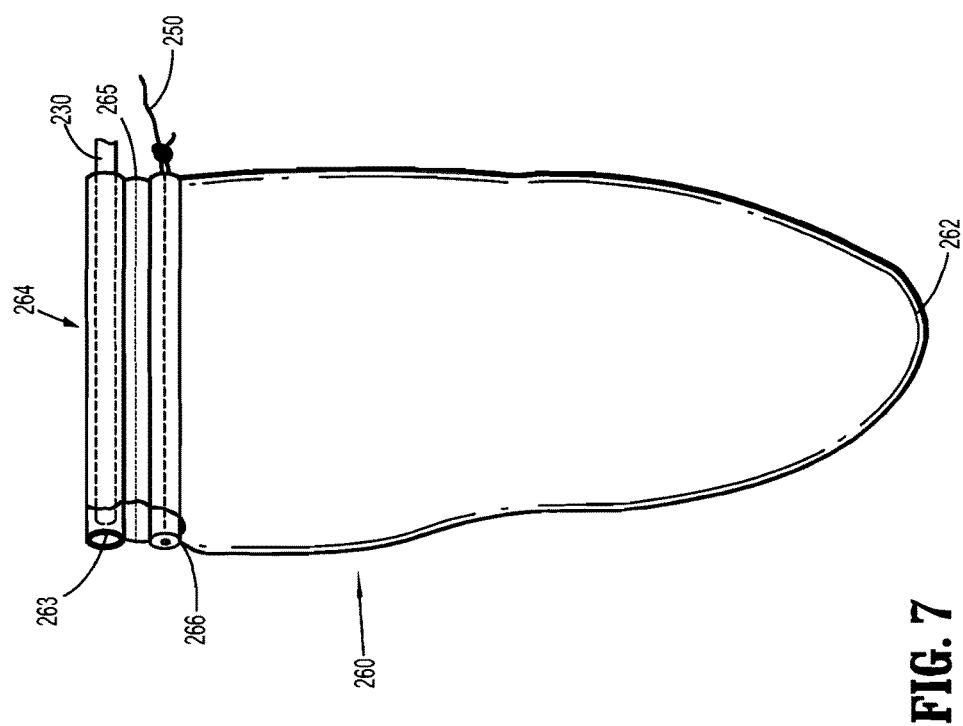
FIG. 7 is a side view of the retrieval pouch of FIG. 6.

One end of a drawstring 250 is attached to finger loop 130, as shown in FIG. 2, while an opposing end of the drawstring 250 is attached to the pouch assembly 260 (FIGS. 2 and 7). In particular, the proximal end of drawstring 250 is attached to ring portion 135 that is releasably coupled to finger ring 130. Drawstring 250 is positioned within a lumen 186 of tubular member 180 (FIGS. 9 and 10). Tubular member 180 slidably houses drive rod 190 and, when undeployed, a pouch support or support member 230 and a pouch 260 (see FIG. 2). Support member 230 includes a resilient spring formed from support arms 231, 232. In the initial, unused condition, pouch 260 will be rolled up and the support member 230, including support portions 231, 232, will be relatively straight and positioned within tubular member 180 (FIGS. 4 and 5). When the drive rod 190 is advanced distally, support member 230 exits the distal end of tubular member 180 and resiliently pops open, thereby deploying and opening pouch 260 attached thereto.

Figure 6:
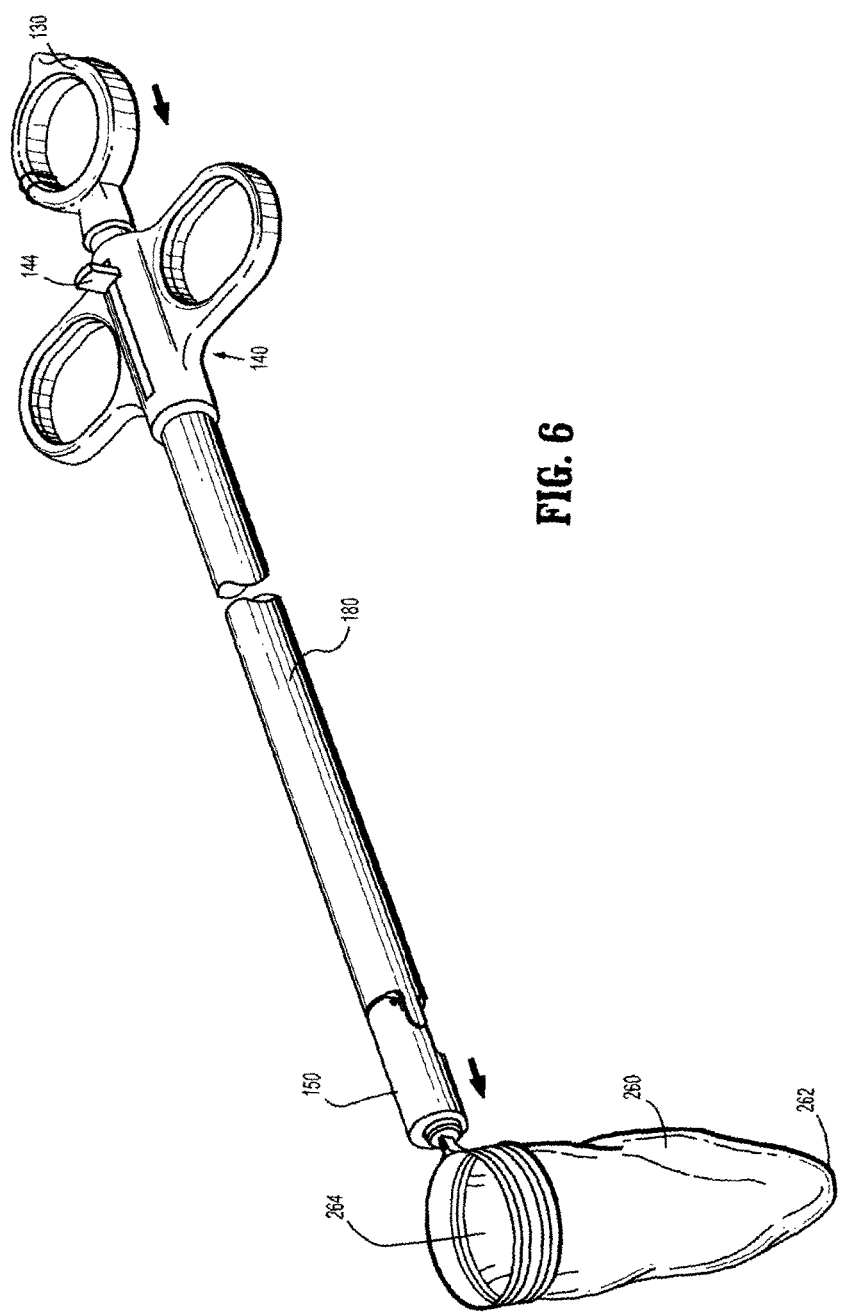
FIG. 6 is a perspective view of the specimen retrieval apparatus of FIG. 1 with a retrieval pouch in a deployed state.
Figure 13:
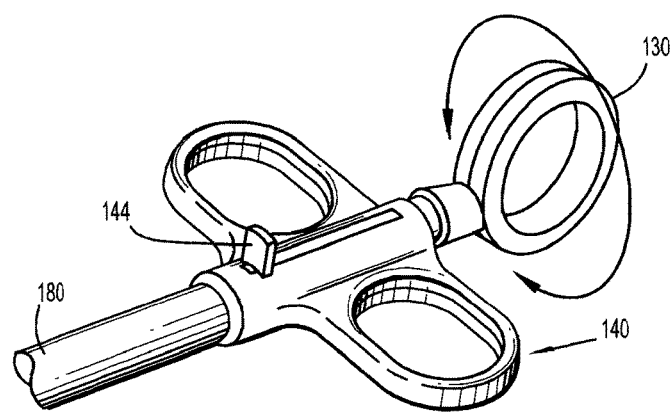
FIG. 13 is a perspective view of the handle of FIG. 11 with a finger loop rotated.
Figure 14:
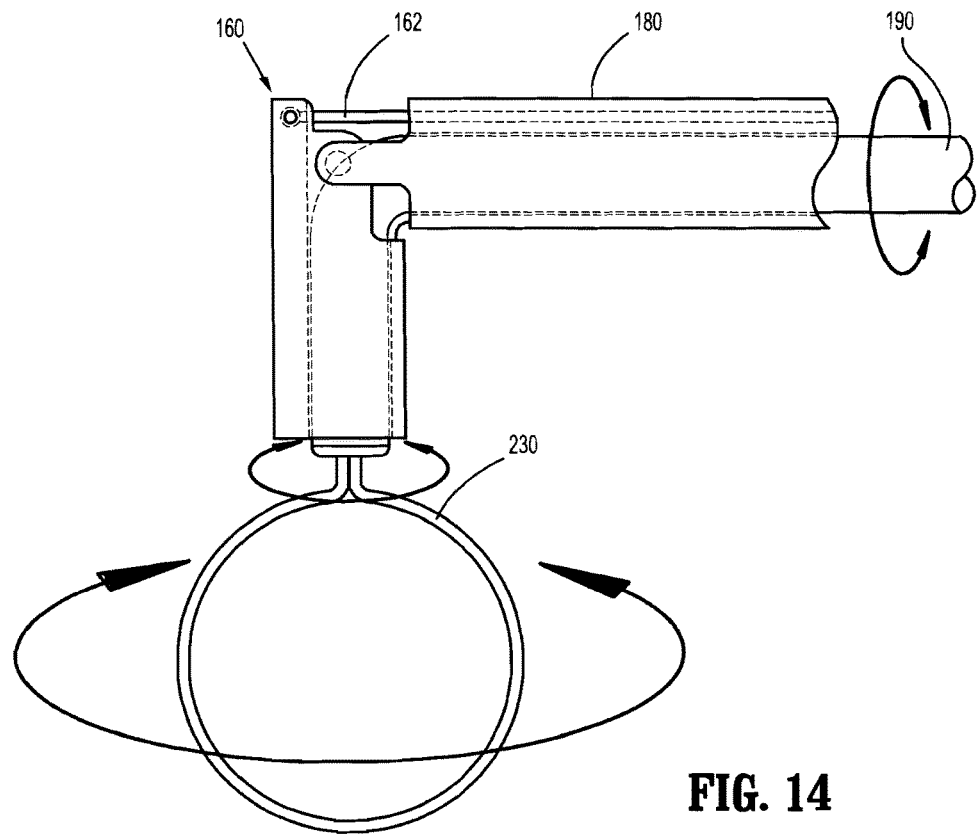
FIG. 14 is a side view of the distal end of the specimen retrieval apparatus of FIG. 1 with the articulation assembly in a second state and illustrating rotation of a support member assembly.

Drive rod or bar 190 is an elongated generally cylindrical member slidably disposed through the bore of tubular member 180. A distal end 191 of drive rod 190 is attached to pouch 260 to move pouch 260 from a non-deployed (retracted) position contained within the outer tubular member 180 (FIG. 4) to a deployed (advanced) position distal to the outer tubular member 180 (and end effector 150) (FIG. 6). Drive rod 190 also includes O-rings 210a, 210b, and 210c to help maintain a drawstring in place while permitting sliding movement of drive rod 190 through tubular member 180. In minimally invasive procedures utilizing insufflation, O-rings 210a-210c help maintain a gaseous seal. In the embodiments illustrated and described that include articulation assemblies and/or flexible portions, at least a portion of drive rod 190 is also flexible. Further still, drive rod 190 is rotatable about the longitudinal axis of tubular member 180 (FIG. 14) in response to rotation of finger loop 130 (FIG. 13) which rotates support member 230 and pouch 260.

A locking tab 105 can be included to prevent premature actuation of the surgical retrieval apparatus 100 during shipping. Locking tab 105 includes snap fit engagement structure to engage a slot of the drive rod 190. When thus engaged, drive rod 190 cannot be pushed distally beyond the point where locking tab 105 engages the proximal end of handle portions 110, 120. To actuate surgical retrieval apparatus 100, the surgeon first disengages locking tab 105 by pulling it off surgical retrieval apparatus 100.

Referring to FIG. 7, pouch 260 includes a flexible film or sheet formed from a substantially transparent polymeric material. Pouch 260 may be formed from a polyurethane sheet, although other biocompatible materials capable of forming a flexible membrane, such as latex, may be used. In one embodiment, pouch 260 is formed from an aromatic polyester type thermoplastic polyurethane such as Dureflex™, a product of Deerfield Urethane, Inc. in Whately, Mass. In addition, the material should be impervious to penetration by cancer cells.

The pouch 260 may be of any dimensions suitable for the purpose of organ entrapment or removal. Pouch 260 includes a closed distal end portion 262 and an openable and closable end portion or mouth 264. Pouch 260 may alternatively include a circumferential concave portion in the vicinity of the open proximal end portion or mouth 264, for facilitating rolling and placement of the pouch 260 within tubular member 180 (FIG. 4). As seen in FIG. 5, a cover 240 can be used to enclose support member 230 and pouch 260 when they are loaded within tubular member 180. Open proximal end portion or mouth 264 is defined by a proximal (upper) circumferential tubular portion or sleeve 263, and a distal (lower) circumferential tubular portion or sleeve 266, which are spaced apart from each other.

Pouch 260 possesses a linear portion 265 weakened by perforation or scoring, which extends circumferentially around mouth 264 of pouch 260 between proximal and distal sleeves 263 and 266, respectively. Scored line 265 may be created by induction heating to create a linear portion having thickness less than that of the original material to facilitate tearing of the material along scored line 265.

Proximal sleeve 263 is adapted to receive support member 230. Distal sleeve 266 is adapted to receive drawstring 250 and extends circumferentially around mouth 264 of pouch 260 forming a loop or pathway for drawstring 250. One end of drawstring 250 may include a knot. Scored line 265 is adapted to tear when drawstring 250 is pulled with sufficient force to close mouth 264 of pouch 260 distal to scored line 265, thereby providing fast detachment of pouch 260 from support member 230 simultaneously with closure of mouth 264. Clearly, alternative structures also can be utilized to detach pouch 260 from support member 230, such as by pulling with a grasper or by cutting with a scissors.

Support member 230 includes two flexible and resilient support portions or arms 231, 232 as discussed above, which, in an unstressed or freely expanded condition, combine to form a generally circular hoop for supporting the periphery of mouth 264 of pouch 260 (in the open configuration). A joiner 233 (FIG. 2) is attached to the distal ends of support portions 231, 232. The distal ends of support portions 231, 232 meet in an opposing relationship where they are attached to each other by joiner 233. Joiner 233 may be a shrink tube. When force is applied to support member 230, support portions 231, 232 move toward each other in a substantially symmetrical manner. When support member 230 is stored inside tubular member 180 (FIG. 4), it is in the closed configuration. Support member 230 is resiliently biased towards the open configuration. Each support portion 231, 232 has a proximal end portion 231a, 232a, respectively, that are adapted to be received into an open end of drive rod 190. Longitudinal movement of drive rod 190 will move support member 230 and attached pouch 260 between the closed configuration and the open configuration. Support member 230 is preferably fabricated from a resilient metal (e.g. stainless steel).

Figure 11:
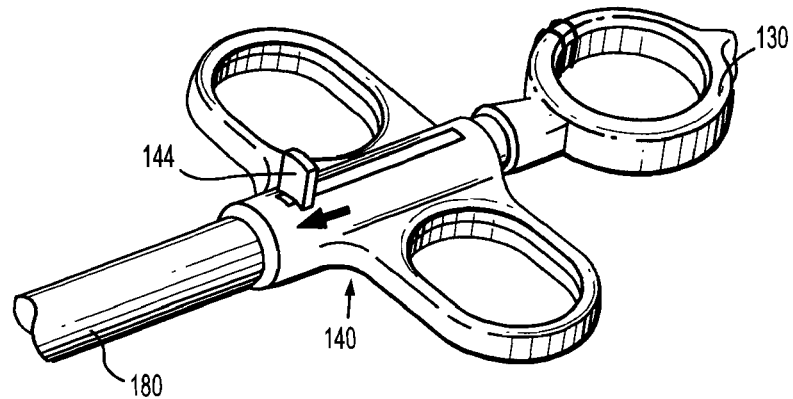
FIG. 11 is a perspective view of the handle of the specimen retrieval apparatus of FIG. 1 with an articulation switch in a second position.
Figure 12:
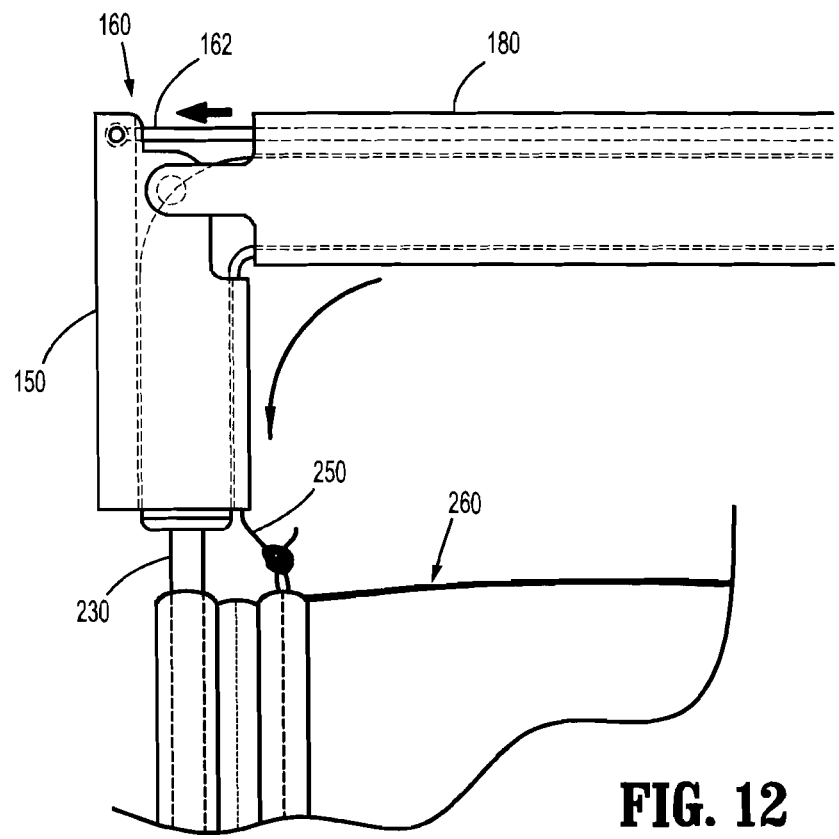
FIG. 12 is a side view of the distal end of the specimen retrieval apparatus of FIG. 8 with the articulation assembly in a second (articulated) state corresponding to the position of the switch in FIG. 11.

Referring now to FIGS. 2, 3, and 8-10, articulation assembly 160 includes a control arm 162. Control arm 162 is slidably disposed in a passage 182 of tubular member 180. A proximal end of control arm 162 is attached to switch 144 and a distal end is connected to end effector 150 via a pin 164. A pair of buttons 183 (FIG. 9) is located on inner surfaces of fingers 185 that extend distally from tubular member 180 (FIG. 8). A corresponding pair of openings 153 is located on end effector 150. When assembled, buttons 183 are rotatably disposed in openings 153 such that end effector 150 is pivotably coupled to tubular member 180. When switch 144 is in its proximal position (FIG. 1), control arm 162 maintains end effector 150 in substantial alignment with a longitudinal axis of tubular member 180. As switch 144 is slid towards its distal position (FIG. 11), it translates control arm 162 through passage 182 and repositions end effector 150 such that end effector 150 defines an angle with respect to the longitudinal axis of tubular member 180 (FIG. 12). Thus, end effector 150 is repositionable and defines a plurality of angles with respect to the longitudinal axis of tubular member 180 that ranges from about 0° to about 90°. In this manner, end effector 150 and pouch 260 are maneuverable, which allows the practitioner greater flexibility in performing a surgical procedure. Further still, end effector 150 includes a passage extending therethrough that is substantially aligned with the bore of tubular member 180.

Figure 17:
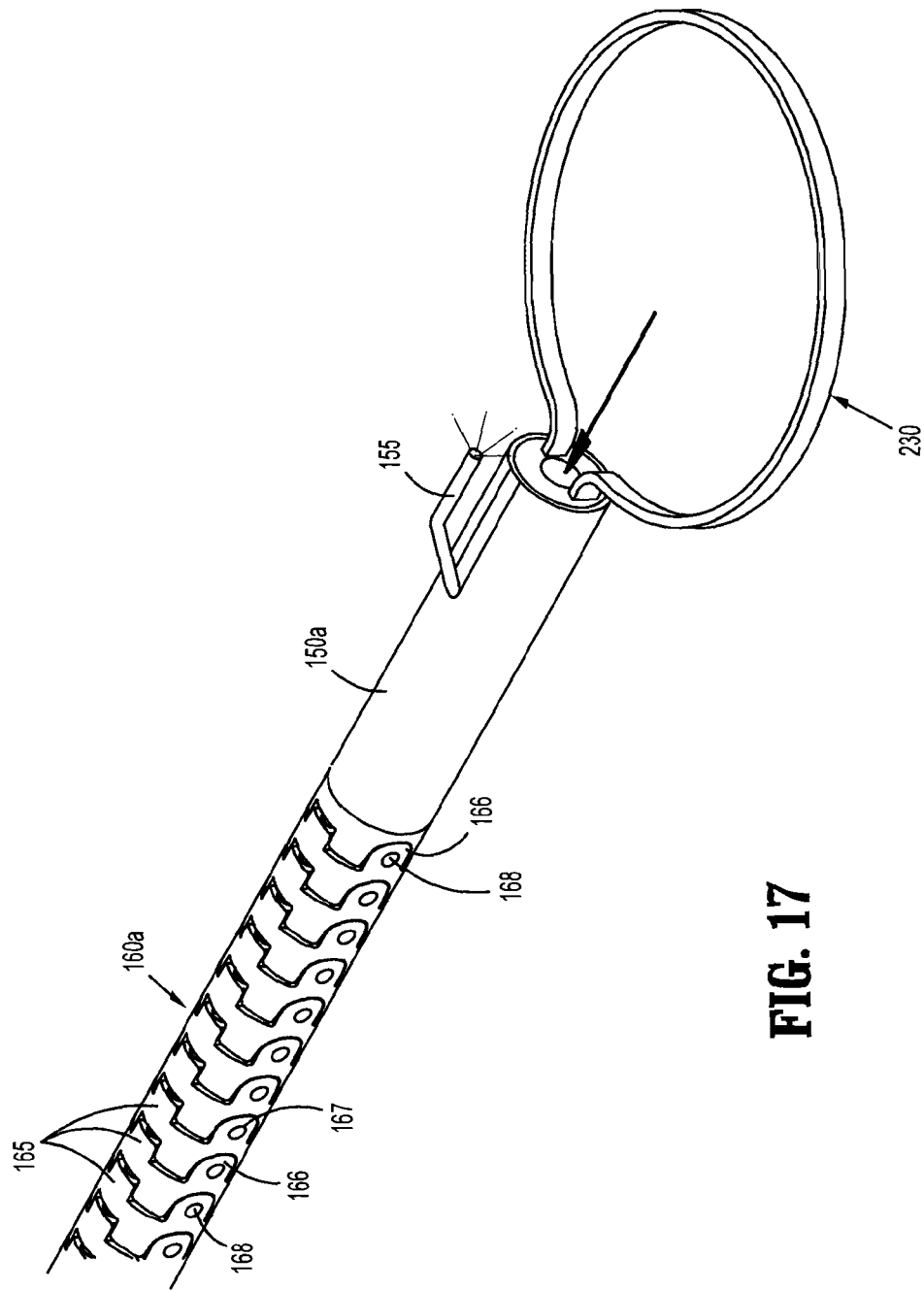
FIG. 17 is a perspective view of a distal end of an alternate embodiment of the presently disclosed specimen retrieval apparatus showing an alternative articulation assembly.

The surgical retrieval apparatus may include other articulation assemblies. Referring now to FIG. 17, an articulation assembly 160a is illustrated. In this embodiment, an end effector 150a is coupled to the distal end of tubular member 180 via articulation assembly 160a. Articulation assembly 160a includes a plurality of segments 165. Each segment 165 is pivotably coupled to an adjacent segment 165. In particular, each segment 165 includes a pair of opposed extensions 166 having openings 167 therein. Openings 167 rotatably receive posts 168 of the adjacent segment 165. A control arm (not shown), that is similar to control arm 162, extends through articulation assembly 160a. A proximal end of the control arm is attached to switch 144 and a distal end of the control arm is attached to an end effector 150a. End effector 150a is substantially similar to end effector 150 that was discussed above. End effector 150a differs in that a proximal end of end effector 150a includes a pair of posts 168 that are rotatably coupled to extensions 166 of segment 165. Further still, end effector 150a includes a tube 155 that is operator controllable for providing an irrigating fluid to the surgical site.

Figure 18:
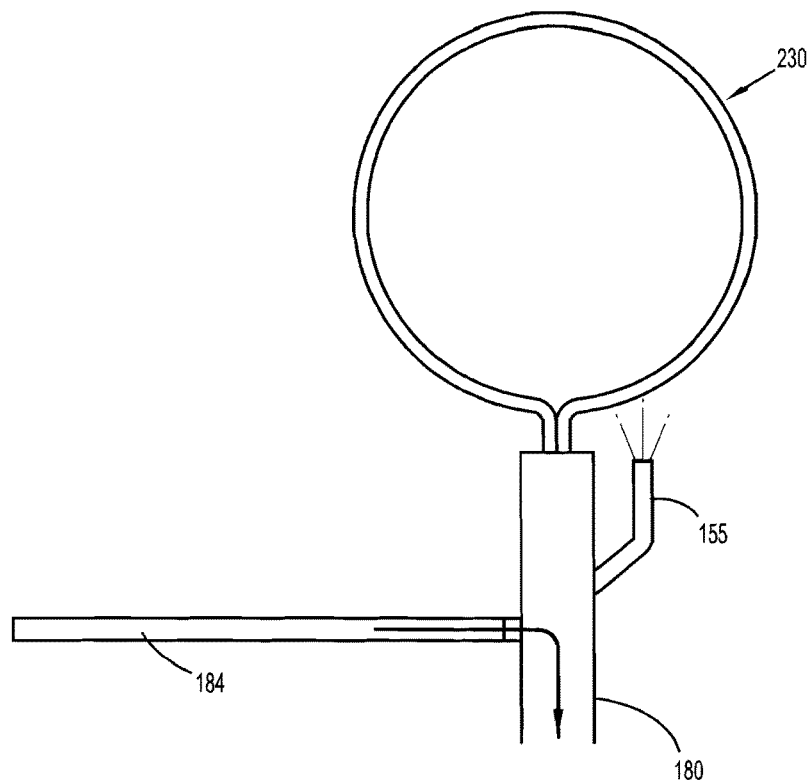
FIG. 18 is a side plan view of a further embodiment of the presently disclosed surgical retrieval apparatus depicting a vacuum line coupled to a distal end of the surgical retrieval apparatus.

In FIG. 18, a further embodiment of the surgical retrieval apparatus is shown. In this embodiment, an extension tube 184 is coupled to a distal end of tubular member 180. Extension tube 184 is fluidly coupled to a source of vacuum (not shown) that is proximal to surgical retrieval apparatus 100. By supplying vacuum to the operative site, the practitioner is capable of removing small specimens or pieces of tissue in addition to capturing tissue specimens or samples in pouch 260. Further still, the vacuum supplied by extension tube 184 may be used to draw tissue specimens towards pouch 260 for facilitating retrieval of the tissue specimens. Tube 155 supplies an irrigating fluid to the surgical site and support member 230 can be rotatable about the longitudinal axis of tubular member 180 and articulatable with respect to tubular member 180 as in the embodiments described herein. It is contemplated that extension tube 184 may be flexible and/or articulable allowing the practitioner to maneuver the distal end of extension tube 184 to a desired location during the surgical procedure.

Figure 22:
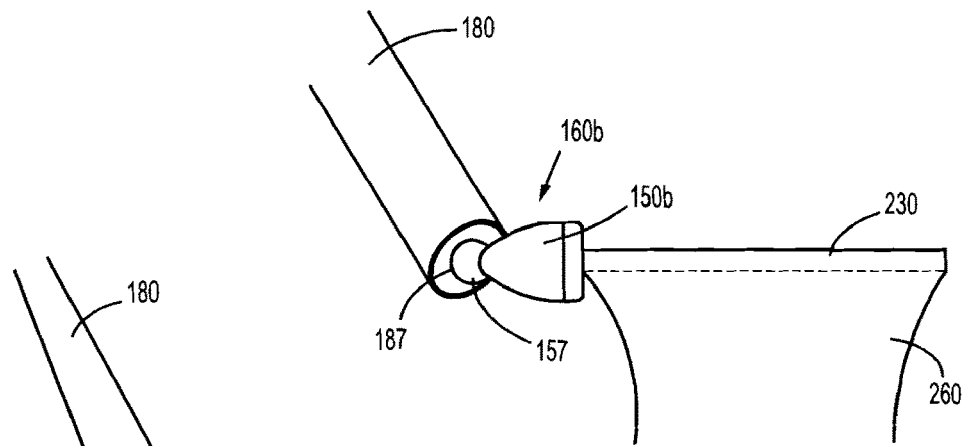
FIG. 22 is a perspective view of a distal end of yet another embodiment of the presently disclosed specimen retrieval apparatus illustrating an alternate articulation assembly.

Alternatively, as seen in FIG. 22, an articulation assembly 160b includes a socket 187 disposed at the distal end of tubular member 180 and a ball 157 attached to a proximal end of end effector 150b. End effector 150b is substantially similar to end effector 150 that was previously discussed and only the differences between them will be discussed in detail. In articulation assembly 160b, a control arm (not shown), that is substantially similar to control arm 162, is slidably disposed in tubular member 180. A proximal end of the control arm is attached to switch 144 and a distal end of the control arm is coupled to ball 157. In this arrangement, axial translation of the control arm rotates ball 157 in socket 187 thus repositioning end effector 150b relative to tubular member 180. Although not illustrated to scale, end effector 150b is configured and dimensioned to receive support member 230 and pouch 260 in their undeployed states. Further still, ball 157 includes a channel (not shown) for receiving an end of drive rod 190 that extends support member 230 from end effector 150b and retracts support member 230 into end effector 150b.

Figure 23:
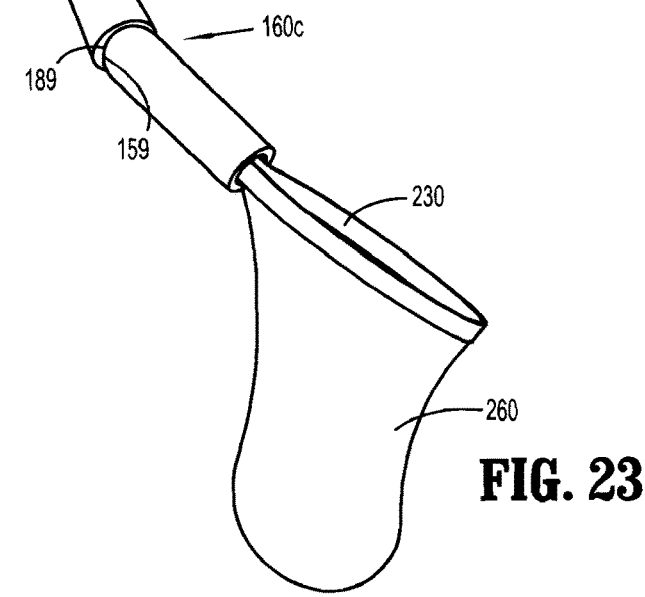
FIG. 23 is a perspective view of a distal end of a further embodiment of the presently disclosed specimen retrieval apparatus illustrating another articulation assembly.

Alternatively, as seen in FIG. 23, articulation assembly 160c includes a recess 189 formed at the distal end of tubular member 180 that rotatably receives a rounded end 159 of end effector 150c. End effector 150c is substantially similar to end effector 150 that was previously discussed and only the differences between them will be discussed in detail. Similar to articulation assembly 160b, a control arm extends through tubular member 180. A proximal end of the control arm is attached to switch 144 and a distal end of the control arm is coupled to a proximal end of rounded end 159. Axial movement of the control arm through tubular member 180 articulates end effector 150c. Recess 189 and rounded end 159 both have openings (not shown) for receiving a distal end of drive rod 190. As in previous embodiments, axial translation of drive rod 190 repositions support member 230 and pouch 260 between deployed and undeployed states.

Figure 24:
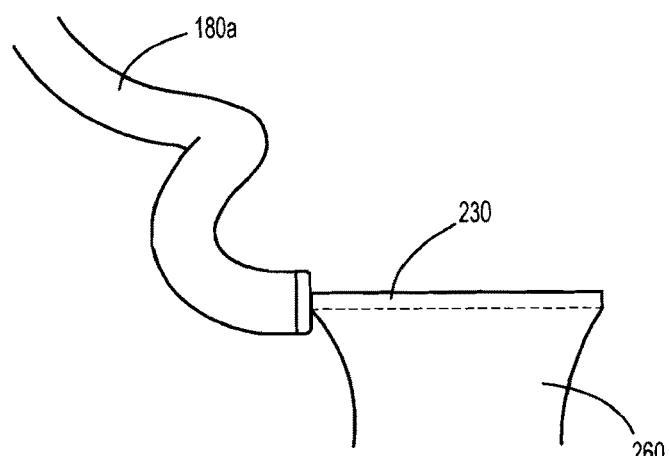
FIG. 24 is a perspective view of a distal end of an alternate embodiment of the presently disclosed specimen retrieval apparatus showing a flexible shaft.

Referring now to FIG. 24, tubular member 180a replaces tubular member 180 of previous embodiments. Tubular member 180a is substantially similar to tubular member 180, with only the differences between them being discussed in detail. At least a portion of tubular member 180a is flexible allowing a distal end thereof to be repositioned in a variety of positions. It is contemplated that the flexible portion of tubular member 180a may be adjusted using a separate tool that is introduced through a separate access port. It is also envisioned that the flexible portion of tubular member 180a may be repositioned using one or more flexible cables disposed within tubular member 180a.

Figure 19:
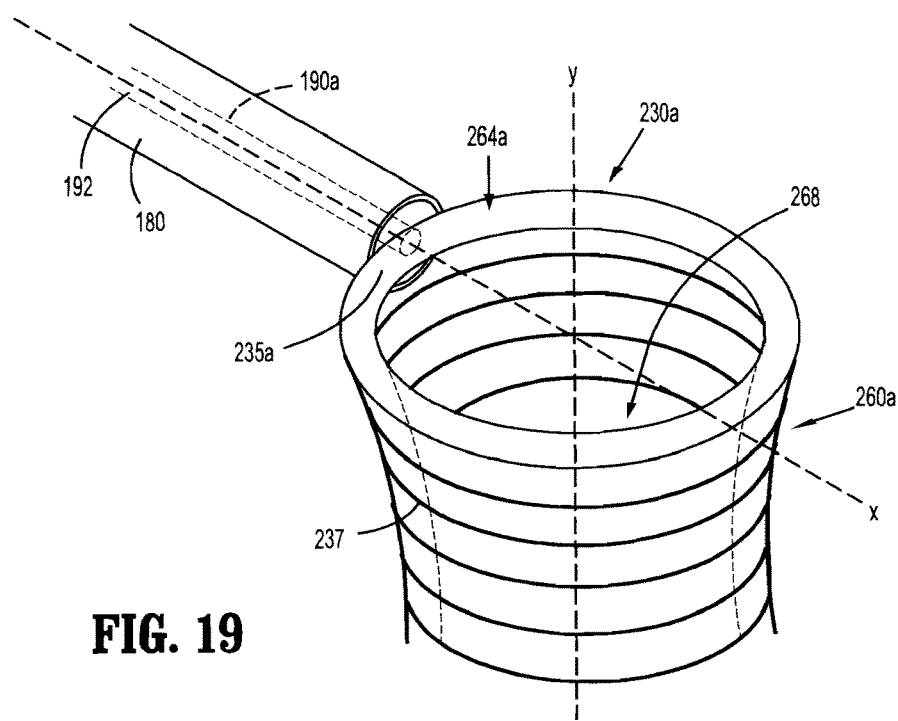
FIG. 19 is a perspective view of an alternate embodiment of a pouch for the presently disclosed surgical retrieval apparatus.

An alternative support member 230a is illustrated in FIG. 19. Support member 230a includes a chamber 235a and is coupled to a distal end of drive rod 190a. Drive rod 190a is substantially similar to drive rod 190 of previous embodiments, with only the differences being discussed in detail. In particular, drive rod 190a includes a central lumen 192 that is in fluid communication with chamber 235a of support member 230a and a source of fluid (not shown) at a proximal end of tubular member 180. Sources of fluid include pressurized gases (e.g. carbon dioxide) or liquids (e.g. saline). Other biocompatible fluids may be used as well.

Further still, support member 230a includes a plurality of splines 237 that are concentrically oriented and define a pouch 260a with a mouth 264a and a cavity 268. The pouch 160a has a closed end opposite the mouth 264a. In particular, support member 230a defines the pouch 260a when an inflation fluid is introduced into chamber 235a between inner and outer walls. Splines 237 provide structural support and help maintain orientation of support member 230a prior to the introduction of the inflation fluid (i.e. similar to support member 230 and pouch 260 of FIG. 4). In particular, support member 230a is an expandable member that is in fluid communication with a source of inflation fluid (not shown) via central lumen 192 of drive rod 190a. As support member 230a expands, it defines mouth 264a and pouch 260a which extends substantially transverse to a longitudinal axis of tubular member 180. Specifically, support member 230a expands substantially circumferentially about axis X, while expanding substantially transverse along axis Y. By providing surgical retrieval apparatus with support member 230a, a separate pouch 260 is not necessary.

Referring now to FIG. 20, an alternate support member 230b is depicted. Support member 230b is an expandable ring having a chamber defined between inner and outer walls thereof. In this embodiment, support member 230b is coupled to a distal end of drive rod 190b and if desired can be configured to be movable between a retracted position within tube 180 and an advanced position extending from the tube 180. Alternately, in the deflated state, it can remain outside the tube 180. In this embodiment, when the practitioner desires to open the mouth of the pouch (not shown), the practitioner introduces the selected fluid into the chamber 235b via central lumen 192a. The fluid causes the support 230b to expand from a collapsed condition to an expanded condition (FIG. 20), thereby opening the mouth of the pouch which is supported by support 230b. The practitioner may also withdraw the fluid from the chamber causing support member 230b to contract and urging the mouth closed. It is envisioned that a source of vacuum may be placed in fluid communication with the chamber such that the practitioner may apply vacuum and cause the mouth to close completely. The expandable ring support member can reduce trauma to surrounding tissue. The inflatable ring allows the practitioner to control the amount of inflation and deflate support member 230b while the support member 230b is distally spaced from the distal end of tubular member 180. This allows the practitioner increased flexibility when performing surgical procedures. Support member 230b may also include one or more lengths of material for reinforcement similar to those employed in support member 230a. The reinforcing material (e.g. metal bands or threads) may be disposed within the chamber or may be incorporated into the walls of support member 230b. By including reinforcing material into the structure of support member 230b, the rigidity of support member 230b is increased while maintaining the flexibility.

Referring now to FIG. 21, an alternate support member 230c is shown. Support member 230c is formed from an expandable foam material. Suitable biocompatible foams are known in the art. Support member 230c is biased towards the open or deployed condition as shown in FIG. 21. When support member 230c is located within tubular member 180, it is in the collapsed condition. Axial movement of drive rod 190c moves support member 230c from within tubular member 180 to a location distal of tubular member 180. Alternatively, in the non-expanded state it can remain outside tubular member 180. Similar to support member 230, as support member 230c exits the distal end of tubular member 180, its natural bias urges support member 230c towards the deployed condition. Alternatively, support member 230c may include a chamber that is coupled to a lumen of drive rod 190c. In this situation, the chamber is in fluid communication with a proximal end of drive rod 190c similar to that discussed hereinabove. This permits the practitioner to introduce a foam material into the chamber, which causes expansion of support member 230c. When using an external source of foam material, support member 230c does not expand to the deployed state upon exiting the distal end of tubular member 180. In this instance, the practitioner deploys support member 230c by axially translating drive rod 190 and subsequently introducing the foam material and expanding support member 230c. A foam material can in some instances provide a more rigid support member than using a gas as in support member 230b.

At times it may become necessary to remove tissue samples or other small amounts of tissue from a patient. Using known techniques, a surgeon makes one or more incisions in the patient's skin. A cannula or other access device is inserted in each of the incisions. The operative site may be insufflated with a biocompatible fluid (e.g. carbon dioxide) if increased space is desired such as in laparoscopic surgery. In other minimally invasive procedures, such as thoracic procedures, where access is provided between adjacent ribs, the cavity is not insufflated. The surgical retrieval apparatus, e.g. apparatus 100, is inserted through one of the cannulas and maneuvered towards the tissue sample to be retrieved. Once surgical retrieval apparatus 100 is in the vicinity of the tissue sample, the surgeon removes locking tab 105, if it has not been previously removed. The surgeon grasps finger ring 130 and moves drive rod 190 distally through tubular member 180. Distal movement of drive rod 190 moves support member 230 and pouch 260 through an open distal end of tubular member 180 and end effector 150. Once support assembly 230 clears the distal end of end effector 150, support assembly 230 opens causing mouth 264 of pouch 260 to open. The surgeon maneuvers pouch 260 towards the tissue sample to be retrieved. Depending on the circumstances, the surgeon may rotate pouch 260 by rotating finger ring 130. Also, the surgeon may reposition end effector 150 off axis by adjusting switch 144, which controls the articulation of end effector 150.

Figure 15:
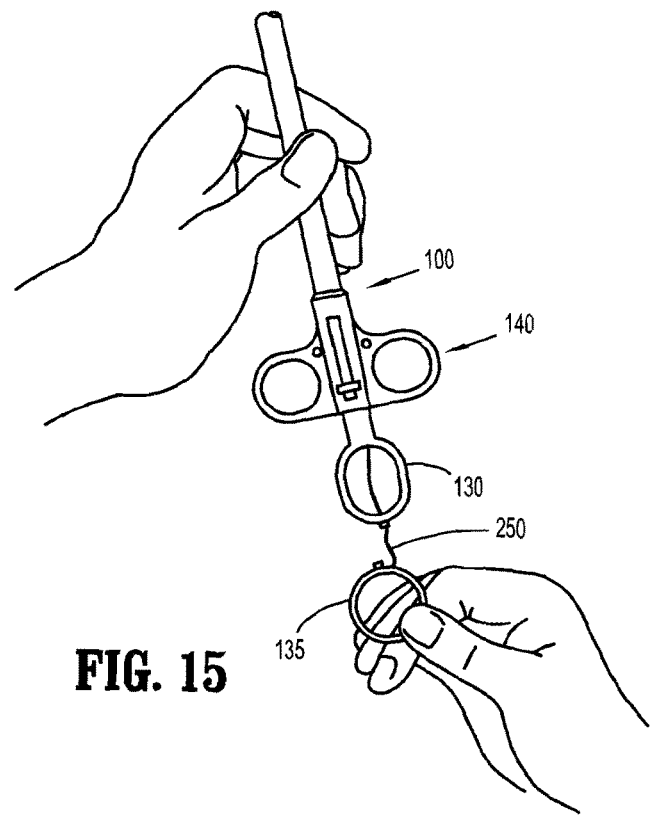
FIG. 15 illustrates cutting a drawstring of the specimen retrieval apparatus.
Figure 16:
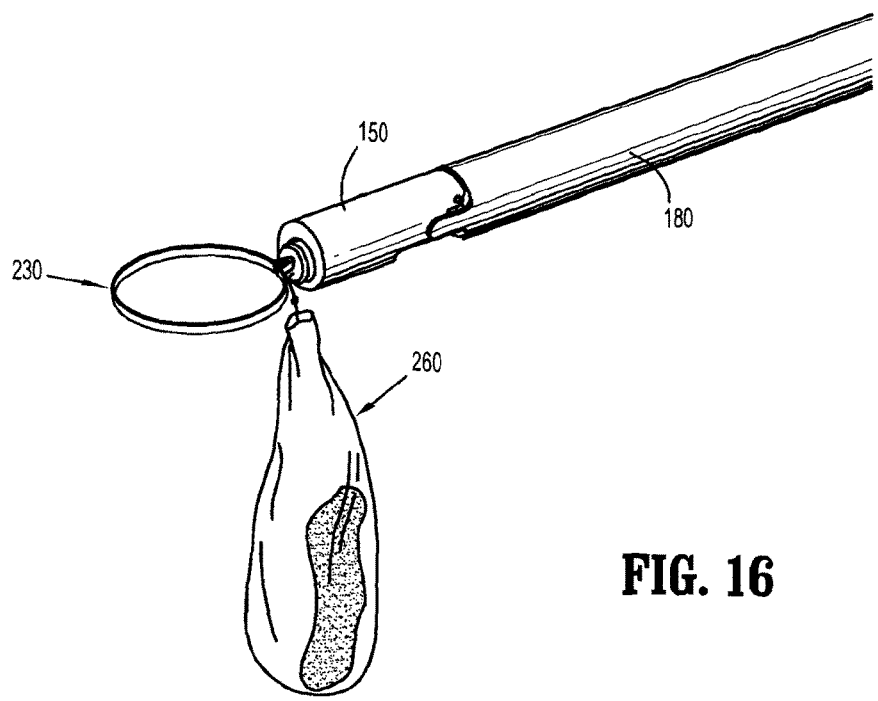
FIG. 16 is a perspective view of the distal end of the specimen retrieval apparatus of FIG. 1 with the retrieval pouch separated from the support member assembly.

Once the tissue sample is located within pouch 260, the surgeon closes mouth 264 by pulling drawstring 250 proximally using ring portion 135. Continued proximal movement of drawstring 250 also separates pouch 260 from support member 230 (FIG. 16). The surgeon cuts drawstring 250 using a knife that is mounted on finger ring 130 (FIG. 15). Through a separate access tube, the surgeon inserts a grasper for retrieving pouch 260. The surgeon grabs drawstring 250 near support assembly 230 and withdraws pouch 260 containing the tissue sample. Surgical retrieval apparatus 100 is then removed from the operative site.

When utilizing the other embodiments of the support assembly, the surgeon will place the pouch about the tissue sample as before. Since these embodiments do not include a drawstring, the surgeon will use other methods, such as a knife or other cutting tool to separate the pouch from the support assembly. In certain instances, the pouch can remain attached and the apparatus removed through the access port or opening.

Although the illustrative embodiments of the present disclosure have been described herein with reference to the accompanying drawings, the above description, disclosure, and figures should not be construed as limiting, but merely as exemplifications of particular embodiments. It is to be understood, therefore, that the disclosure is not limited to those precise embodiments, and that various other changes and modifications may be effected therein by one skilled in the art without departing from the scope or spirit of the disclosure.

What is claimed is:

1. A surgical retrieval apparatus, comprising:
an elongate tubular member defining a bore and a first longitudinal axis, the elongate member having a distal end and a proximal end;
an end effector defining a second longitudinal axis and having a tubular configuration pivotally coupled to the distal end of the elongated tubular member, the end effector having a proximal end and a distal end and being repositionable between a first position in which the second longitudinal axis is aligned with the first longitudinal axis and a second position in which the second longitudinal axis defines an acute angle with respect to the first longitudinal axis;
an articulation assembly including a control arm having a distal end pivotally connected to the end effector, the control arm being movable to move the end effector between the first position and the second position;

a support member movably supported within the end effector, the support member being movable between a retracted position located at least partially within the end effector and a distal position extending from the distal end of the end effector; and a pouch attached to the support member, the pouch being positioned within the end effector when the support member is in the retracted position;

wherein the elongate tubular member defines a passageway extending from the distal end of the elongate tubular member to a handle secured to the elongate tubular member, the control arm extending through and being movable within the passageway to move the end effector between the first and second positions.

2. The surgical retrieval apparatus of claim 1, further including a drive member slidably disposed within the bore of the elongate tubular member, the drive member being movable within the bore to move the support member between the retracted and distal positions.

3. The surgical retrieval apparatus of claim 2, wherein the support member is secured to the distal end of the drive member, the support member having a circular hoop configuration in an unstressed condition.

4. The surgical retrieval apparatus of claim 3, wherein the support member includes two resilient support portions that define the circular hoop configuration.

5. The surgical retrieval apparatus of claim 3, wherein the support member includes an expandable member formed from an expandable foam.

6. The surgical retrieval apparatus of claim 1, wherein the pouch has a first end and a closed second end, the first end being transitionable between an open configuration and a closed configuration.

7. The surgical retrieval apparatus of claim 1, wherein the handle includes a switch coupled to the control arm, the switch being movable to move the control arm to reposition the end effector between the first and second positions.

8. The surgical retrieval apparatus of claim 1, wherein the support member is rotatable about the first longitudinal axis.

9. The surgical retrieval apparatus of claim 1, further including a drawstring positioned about the first end of the pouch, the drawstring being movable to transition the first end of the pouch from the open configuration to the closed configuration.

10. The surgical retrieval apparatus of claim 1, wherein the distal end of the elongate tubular member includes a pair of opposing fingers, the proximal end of the end effector being pivotally coupled to the distal end of the elongate tubular member between the pair of opposing fingers.

11. The surgical retrieval apparatus of claim 10, wherein each of the fingers include an inwardly extending button and the end effector defines spaced openings, wherein each of the buttons is received in a respective one of the spaced openings to pivotally secure the end effector to the elongate tubular member.

12. The surgical retrieval apparatus of claim 1, wherein the pouch is removably supported on the support member.

13. The surgical retrieval apparatus of claim 1, wherein the support member includes an expandable member having a chamber, the expandable member transitioning from a first condition to a second condition upon introduction of a fluid to the chamber.

14. The surgical retrieval apparatus of claim 1, further including a tube coupled to a source of irrigation fluid.

15. The surgical retrieval apparatus of claim 1, further including an extension tube coupled to a source of vacuum.

16. The surgical retrieval apparatus of claim 2, further including socket formed at the distal end of the elongate tubular member and a ball attached to the proximal end of the end effector, the ball being rotatably received within the socket.

17. The surgical retrieval apparatus of claim 16, wherein the ball defines a channel configured to receive the drive member.

18. The surgical retrieval apparatus of claim 17, wherein control arm is attached to the ball such that movement of the control arm effects rotation of the ball within the socket.

* * * * *